United States Patent
Perez

(10) Patent No.: US 7,763,059 B2
(45) Date of Patent: Jul. 27, 2010

(54) UV LIGHT THERAPY DELIVERY APPARATUS

(76) Inventor: Thomas Perez, 3535 W. Irving Park Rd., Chicago, IL (US) 60618

( * ) Notice: Subject to any disclaimer, the term of this patent is extended or adjusted under 35 U.S.C. 154(b) by 56 days.

(21) Appl. No.: 12/186,698

(22) Filed: Aug. 6, 2008

(65) Prior Publication Data

US 2008/0294227 A1    Nov. 27, 2008

Related U.S. Application Data

(63) Continuation-in-part of application No. 11/140,272, filed on May 27, 2005, now abandoned, which is a continuation-in-part of application No. 11/076,169, filed on Mar. 9, 2005, now abandoned, which is a continuation-in-part of application No. 10/926,209, filed on Aug. 25, 2004, now abandoned.

(60) Provisional application No. 60/503,678, filed on Sep. 17, 2003.

(51) Int. Cl.
*A61N 5/06* (2006.01)
*A61B 1/06* (2006.01)

(52) U.S. Cl. .................. 607/94; 607/88; 607/90; 362/572

(58) Field of Classification Search ............ 606/13, 606/14, 16; 607/88, 90–92; 362/157, 158, 362/166–182, 184, 186–189, 197–200, 208, 362/572
See application file for complete search history.

(56) References Cited

U.S. PATENT DOCUMENTS

| | | | | |
|---|---|---|---|---|
| 838,950 A * | 12/1906 | Coger et al | ............ | 607/92 |
| 861,019 A * | 7/1907 | Coger | ............ | 607/92 |
| 1,939,413 A * | 12/1933 | Robinson | ............ | 607/92 |
| 2,034,388 A * | 3/1936 | Cemach | ............ | 607/92 |
| 2,326,773 A * | 8/1943 | Floyd | ............ | 313/48 |
| 2,533,955 A * | 12/1950 | Pitts | ............ | 607/92 |
| 4,676,231 A * | 6/1987 | Hisazumi et al. | ............ | 600/108 |
| 5,304,172 A * | 4/1994 | Manoukian et al. | ............ | 606/15 |
| 5,908,418 A * | 6/1999 | Dority et al. | ............ | 606/40 |
| 6,200,134 B1 | 3/2001 | Kovac et al. | | |
| 6,790,205 B1 | 9/2004 | Yamazaki et al. | | |
| 7,147,654 B2 * | 12/2006 | Baumgardner et al. | ............ | 607/88 |
| 2001/0041887 A1 * | 11/2001 | Crowley | ............ | 606/14 |
| 2003/0097122 A1 | 5/2003 | Ganz et al. | | |
| 2004/0002744 A1 * | 1/2004 | Dungan | ............ | 607/88 |
| 2004/0248059 A1 | 12/2004 | Katsuda et al. | | |
| 2005/0064371 A1 | 3/2005 | Soukos et al. | | |
| 2005/0107849 A1 | 5/2005 | Altshuler et al. | | |
| 2005/0177208 A1 | 8/2005 | Irwin | | |
| 2006/0167531 A1 | 7/2006 | Gertner et al. | | |
| 2006/0195165 A1 * | 8/2006 | Gertner et al. | ............ | 607/86 |

* cited by examiner

*Primary Examiner*—David Shay
(74) *Attorney, Agent, or Firm*—Adam K. Sacharoff; Much Shelist

(57) ABSTRACT

In light therapy apparatus is defined to include a UV light source secured to a casing. A shroud is placed over an exposed portion of the UV light source and is secured or attached around the perimeter of the casing end. Since the UV light source can generate a significant amount of heat, the casing includes an internal fan. Various tubing configurations may be used to help direct the air flow from the fan around the UV light source. In addition, a vent opening in the shroud was found to reduce the temperature of the shroud to prevent damage to a person using the apparatus.

10 Claims, 4 Drawing Sheets

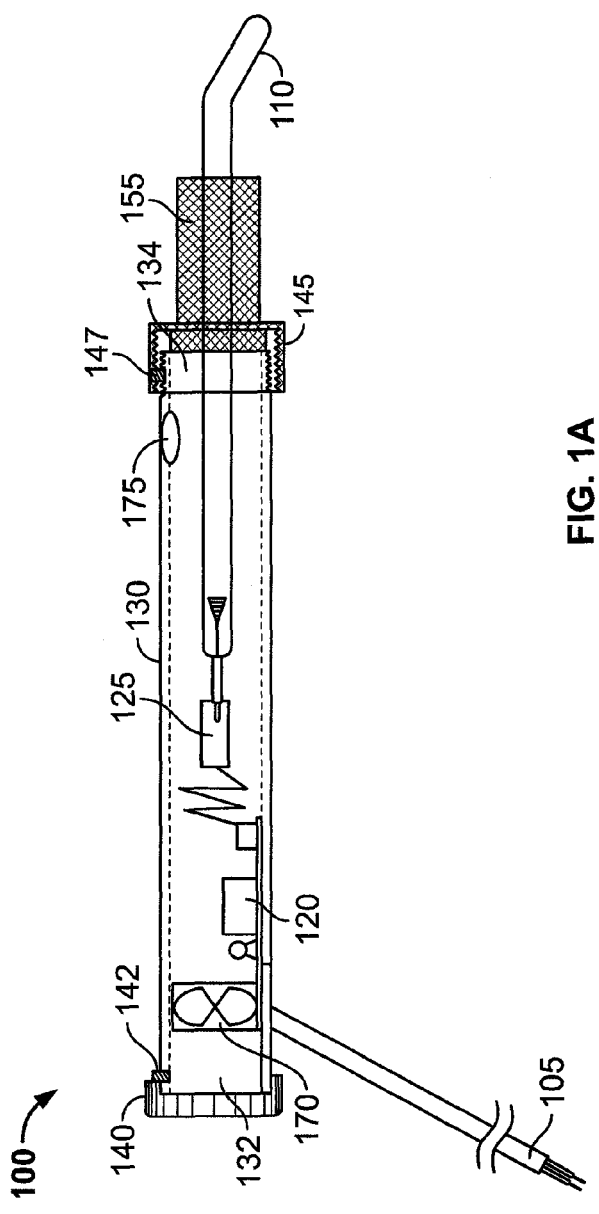
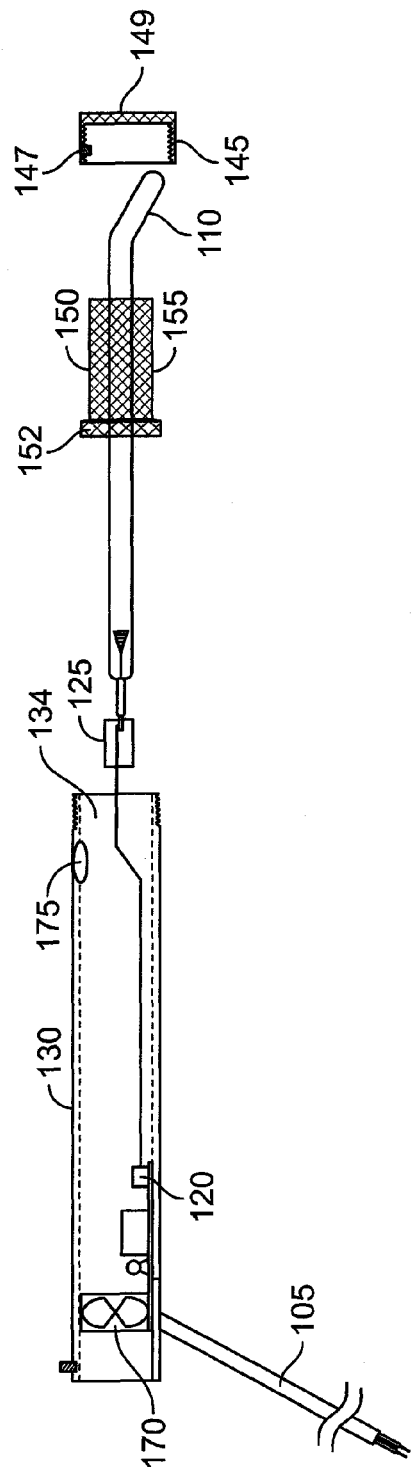
FIG. 1A
FIG. 1B

UV LIGHT THERAPY DELIVERY APPARATUS

CROSS REFERENCE TO RELATED APPLICATIONS

The present application is a continuation in part of U.S. Ser. No. 11/140,272, which in a continuation-in-part of U.S. Ser. No. 11/076,169, which is a continuation-in-part of U.S. Ser. No. 10/926,209, which claimed priority to provisional application Ser. No. 60/503,678.

FIELD OF THE INVENTION

The present invention relates to an improved light therapy delivery apparatus.

BACKGROUND OF THE PRIOR ART

Ultraviolet (UV) light can be used to treat a multitude of medical problems, including for example bacterial, viral and fungal infections, poisoning, fatigue, Alzheimer's disease, allergies and asthma, rheumatic diseases and arthritis, diabetes, hepatitis, and cancer, because UV light sterilizes the blood and acts as an antibiotic. The UV light is applied either to the patient's skin or directly to the blood. If the UV light is applied to the skin it is typically provided to the patient's skin either with a wrap or lamp.

Applying the UV light directly to a patient's blood supply is known as photoluminescence or UV blood illumination (UBI). UV blood illumination increases oxygen, destroys toxins and boosts the immune system. In prior art UBI, a small amount of blood is drawn from the patient, up to about 250 cc. The blood that is drawn travels through a cuvette or glass chamber. The blood is repeatedly illuminated with UV light and then returned to the body. The process is repeated, typically a day or several days later. These treatments are time consuming, and require regular trips to a medical facility. In addition, trained personal must be available to provide the treatments.

Because of the problems associated with UBI, a need developed for providing UV light to a patient's blood without having to draw blood. Meeting this need numerous prior art references disclosed the application the light sublingual with the use of mouth guards, toothbrushes, and elongated light tubes. However, these have proven to be not very effective because of specific problems associated with the materials used and the applications themselves.

It is well known that certain UV light cannot penetrate certain plastics and resins. In addition, trying to force the UV light down a tube towards an eyelet or window was also shown to diminish the UV light. Specific light guides can be employed to communicate the UV light down a tube without diminishing the UV light characteristics. But rather then employ additional material or costs, it has also been suggested to place the source of the UV light at the end of the applicator. The type of UV light source can effect the applicator greatly. For example, the use of a cold cathode tube to supply the UV light source can radiate a lot of heat, having a working temperature of about 101° F. This temperature range is dangerous and harmful to the user, especially when the applicator end is placed sublingually or rectally.

There is one embodiment of the present invention which addresses the need for an apparatus that includes a UV light source which when in use keeps the apparatus within a temperature range that would not be harmful to the user.

SUMMARY OF THE INVENTION

In an embodiment of the invention there is provided a light therapy apparatus. The apparatus includes a main casing having front and rear ends; a light source inserted through the front end of the main casing; a front cap having a central bore for receiving the light source and having a treaded internal structure for securing the front cap to corresponding threaded external structure on the front end of the main casing; a secondary casing having a base end positioned within the front cap and over the front end of the main casing, the secondary casing further including a shoulder section extending outwardly from the base end out of the front cap to partially cover a section of the light source; a shroud placed over the exposed portion of the light source and having at least a flexible bottom end for tightly fitting over an end of the shoulder section, the shroud being made of a light-resistance material to prevent light from the light source from penetrating the shroud; a lens positioned through the shroud to direct light from the light source out of the shroud; and a fan positioned within the casing and directed to transmit air flow to the shroud.

In other embodiments the shroud may include a rigid portion covering the light source; may be further defined as having a base portion extending upwardly to form a tubular shaped covering that terminates into a top portion, the tubular shaped covering includes a front portion, a back portion, and a pair of side portions, the front portion extends inwardly from the base to a concave section, and the back portion extends inwardly from the base to a concave section, the tubular shaped covering is bent away from the base portion at an angle of about 25-35°; or may include an internally defined annular flange extending radially inward that would come into contact with the shoulder section when the shroud is placed thereover.

In yet other embodiments, the casing includes an air intake aperture and/or the shroud could include an air exhaust aperture. Other embodiment may use cooling tubes to help direct the air flow from the fan.

Numerous advantages and features of the invention will become readily apparent from the following detailed description of the invention and the embodiments thereof, and from the accompanying drawings.

BRIEF DESCRIPTION OF THE DRAWINGS

A fuller understanding of the foregoing may be had by reference to the accompanying drawings, wherein:

FIG. 1a is an illustration of an apparatus for light therapy in accordance with a first embodiment;

FIG. 1b is a partially exploded view of FIG. 1a;

FIG. 2b is a sectional view of the apparatus in FIG. 2a;

FIG. 2c is a side view of the apparatus in FIG. 2a;

DETAILED DESCRIPTION OF THE INVENTION

Figure 2A:
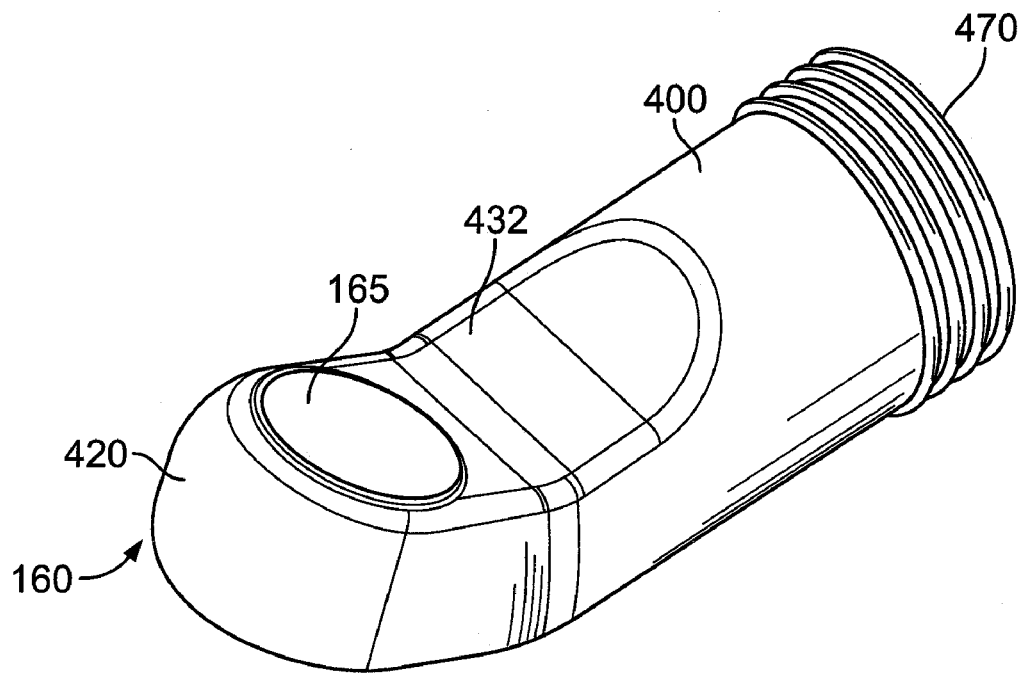
FIG. 2a is a perspective view of a shroud used to cover a light source for a light therapy apparatus.
Figure 2B:
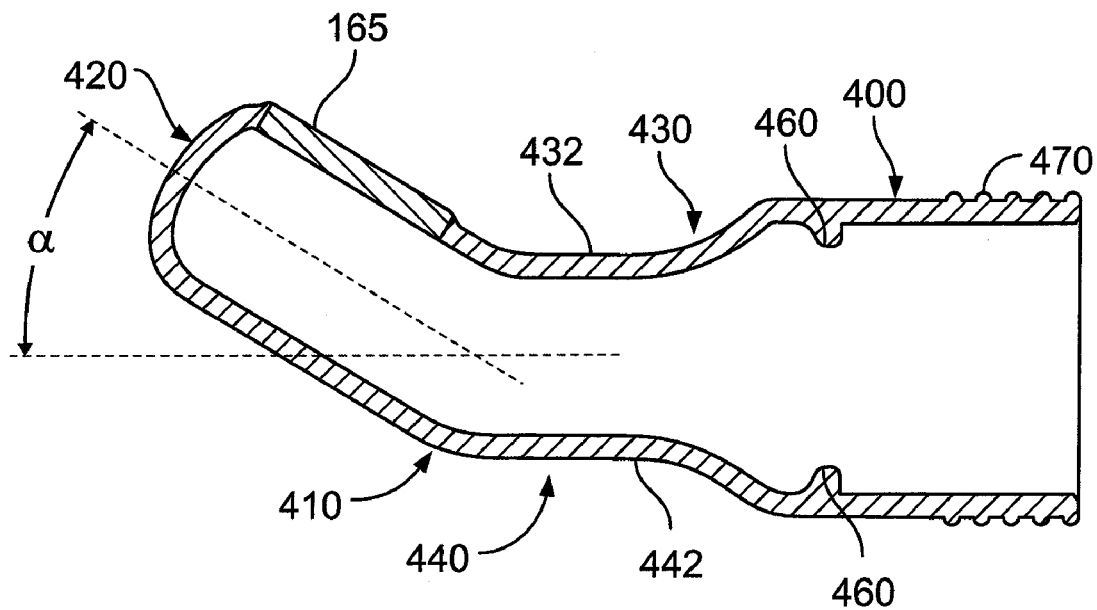
Figure 2C:
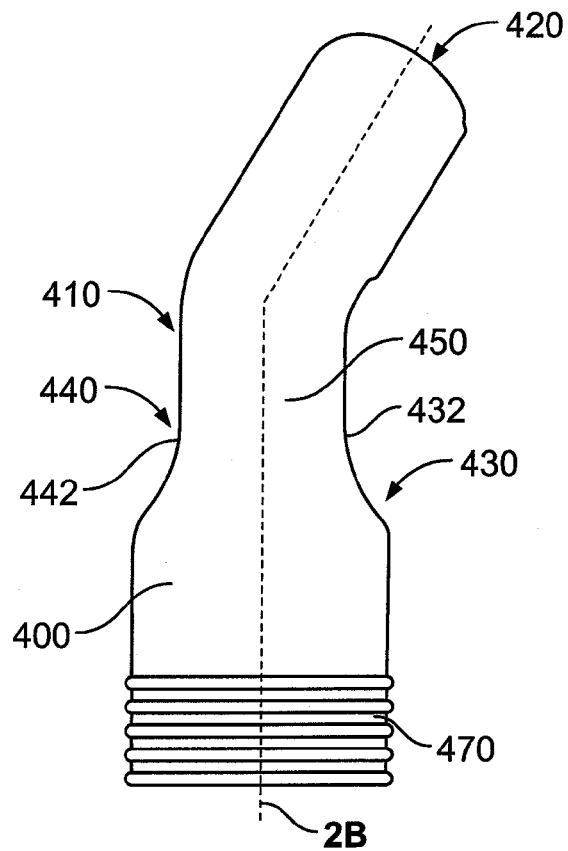
Figure 2D:
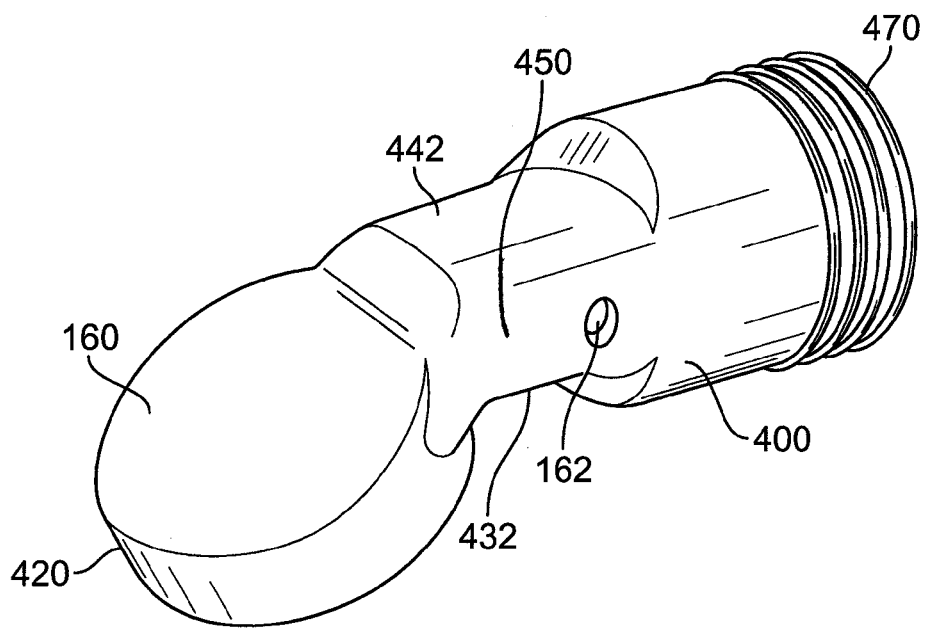
FIG. 2d is a side perspective view of another embodiment of a shroud.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the claims by the embodiments illustrated.

Referring to FIGS. 1a and 1b, there is shown an apparatus 100 for the delivery of UV light to a patient. Ultraviolet light can be used to treat many diseases including infections, poisoning, fatigue, allergies, hepatitis, cancer and HIV. UV light increases the oxygen combining power of the blood, destroys toxins, viruses, fungi, bacteria, and boosts the immune system. UV light also sterilizes the blood and acts as an antibiotic. Preferably, UV light at one or more therapeutic wavelength is utilized in the present invention. More preferably the light is either UV-A or UV-C light is utilized in the present invention. For some conditions and/or diseases UV-A light is more effective than UV-C and for other conditions and/or diseases UV-C light is more effective than UV-A light. The wavelengths or wavelengths of light to be used to treat the patient are selected based on the wavelength or wavelength that will best treat the condition or disease of the patient.

The apparatus 100 is preferably designed to allow a patient to administer the UV light sublingual, under the tongue. The capillaries under the tongue are close to the surface. These capillaries are very sensitive. Capillary exposure of the mucous membrane is significantly greater than other exposed body surfaces. The greater capillary exposure allows for greater penetration of the ultraviolet spectrum. It is also believed that similar exposure can happen rectally.

The apparatus 100 is attached to a power supply (not shown) by power cord 105. The power supply may simply plug directly into an AC outlet and/or utilize a DC converter. This is not an important aspect of the embodiments. The apparatus 100 includes a UV light source 110, which for this embodiment includes a cold cathode UV bulb. The light source 110 is connected to a circuit board 120 by a connector 125, which is preferably a polarized connector. The circuit board 120 would typically include a controller/software and timing mechanism with commands to turn the light source on/off, control the length of treatment time in a given time period, etc.

The apparatus 100 includes a main casing 130 to house the components. The main casing 130 includes a rear cap 140 that may be treaded onto the rear end 132 of the main casing 130. A rear set screw 142 is used to secure the rear cap 140 onto the rear end 132.

The light source is inserted through the front end 134 of the main casing 130 and is secured in place by a front cap 145 that may be threaded onto the front end 134. Similarly, a front set screw 147 is used to secure the front cap 145 onto the front end 134.

The front cap 145 includes a central bore 149 such that it can slide over the UV light source 110 and slide over a secondary casing 150. The secondary casing 150 is captured and secured to the main casing 130 because the secondary casing 150 includes a base end 152 that has a larger diameter then the diameter of the central bore 149. Extending from the base end 152 of the secondary casing 150 is a shoulder section 155 that covers a portion of the UV light source 110. The base end 152 also has a larger diameter than the shoulder section 155.

A shroud 160 (illustrated in FIGS. 2A-2D) is placed over the exposed portion of the UV light source 110 and secured or attached around the perimeter of the shoulder section 155. The shroud 160 is rigid such that the shroud can maintain its shape and such that it does not come into contact with the UV light source 110. As mentioned the UV light source can generate a significant amount of heat. To help protect the user the shroud 160 includes an internal cavity that positions the interior material a distance away from the UV light source. The shroud 160 may be disposable such that a replacement shroud 160 can be used for the next treatment. Alternatively, the shroud 160 may be easily removable and washable. Further details of the shroud are discussed below.

In one embodiment the shroud 160 further includes a lens 165 to allow the UV light source 110 to exit. When the shroud 160 incorporates the lens 165, the rest of the shroud 160 would preferably be made of a photo-resistant or other like material. This helps ensure that the UV light is properly directed out of the shroud at a pre-determined section.

To cool down the area of contact between the apparatus and the user, a fan 170 is inserted near the rear end 132 of the casing 130. The fan 170 is controlled by the circuit board 120. The fan 170 directs air through the casing 130 into the front cap 145 and down the shroud 160 and acts to cool the UV light source 110. An air intake aperture 175 is positioned on the casing 130 near the front end 134.

Figure 3:
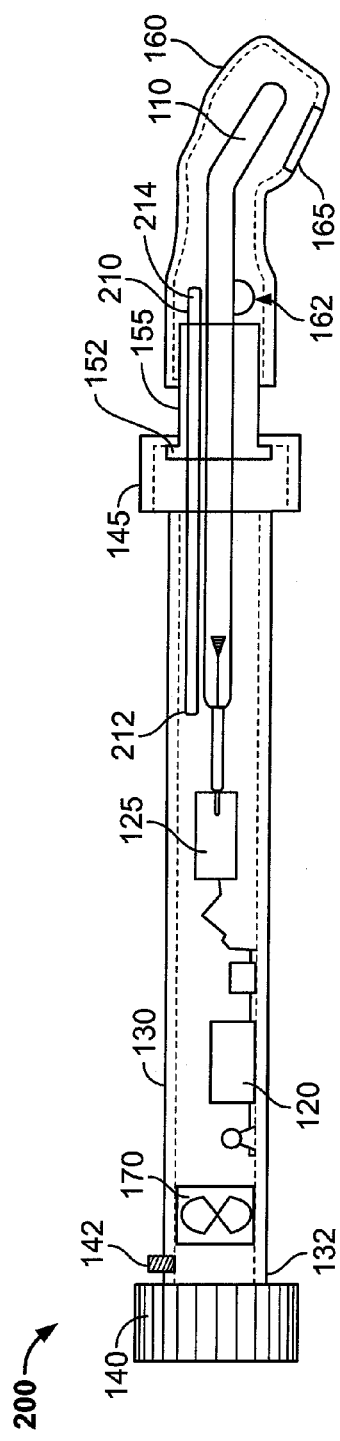
FIG. 3 is an illustration of an apparatus for light therapy in accordance with another embodiment.

Referring now to FIG. 3, in another embodiment the apparatus 200 includes similarly marked components but also includes a cooling tube 210 to help direct the air flow from the main casing 130 through the secondary casing 155 and into the shroud 160—towards the end of the UV light source 110. The cooling tube 210 includes a first opened end 212 positioned within the main casing 130 and includes a second opened end 214 positioned within the shroud 160.

It was further determined that even with the fan and a cooling tube, that the end of the shroud 160 may still be too hot for insertion into and/or to make contact with a portion of a user's body that is 101° F. However, by placing an outlet opening 162 on the shroud 160 in a position apposite the second opened end 214 of the cooling tube 210, that the temperature of the shroud 160 was reduced to a temperature of about 88° F., a working temperature that permits the surface of the shroud to come into contact with the user's body without harming or burning the user.

Figure 4:
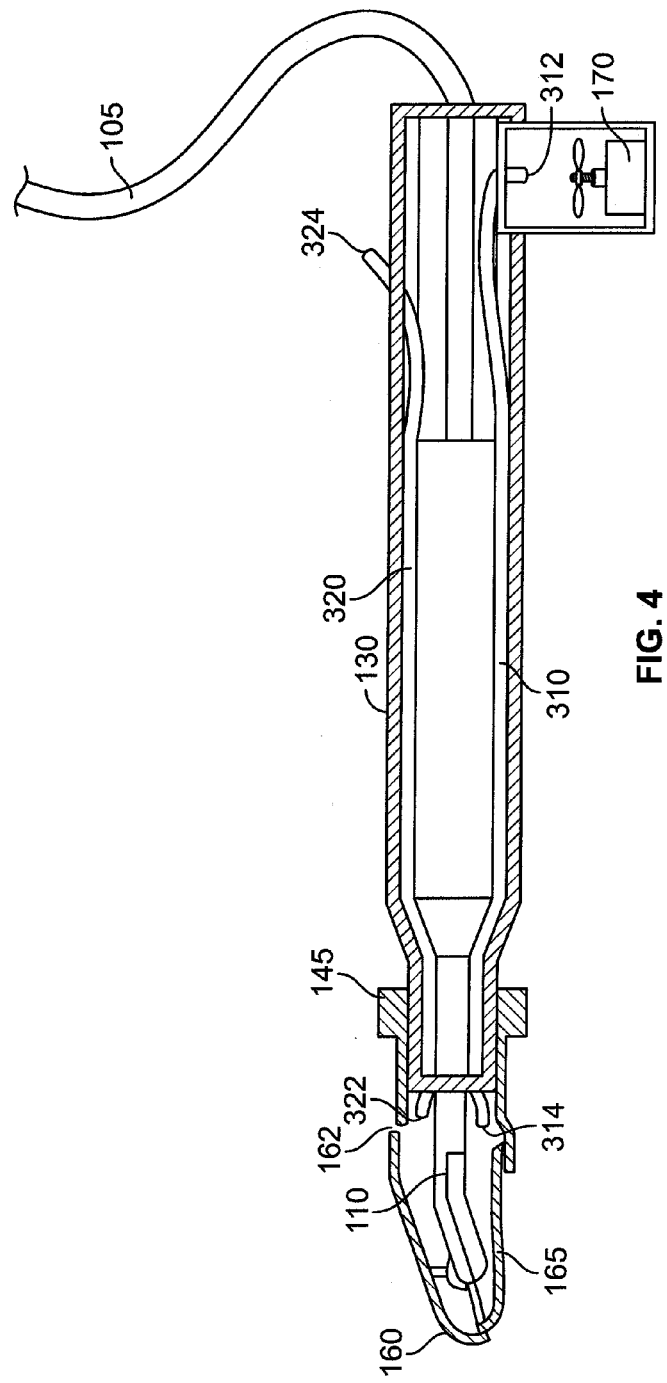
FIG. 4 is an illustration of an apparatus for light therapy in accordance with another embodiment.

Referring now to FIG. 4, in another embodiment the apparatus 300 includes similarly marked components but includes a pair of cooling tubes 310 and 320. The first cooling tube is referred to as a cooling input tube 310 and it includes a first end 312 that is positioned near the fan 170 and includes a second end 314 that is positioned within the shroud 350. The second cooling tube is referred to as a heat output tube 320. The heat output tube 320 includes a first end 322 that is positioned within the shroud 350 and includes a second end 324 that exhausts out of the casing 130. The second end 314 of the cooling input tube 310 and the first end 322 of the heat output tube 320 are positioned at diametrical opposite positions in the shroud, such as, but not limited, the bottom and the top portions of the shroud 350. In addition the shroud 160 could further include an outlet opening 162 to help vent air that has become heated from contact with the UV light source.

Referring back to FIGS. 2A-2D, the shroud 160 as mentioned can include a lens 165 that permits the UV light to penetrate therethrough for the treatment of the blood. The lens is preferably made of a fused quartz material, such as but not limited to GE Type 124 Fused Quartz.

The shroud 160 may also include an outlet opening 162 to help vent the heated air circulating around the UV light source. The shroud 160 may be further defined as having a base portion 400 that extends upwardly to form a tubular shaped covering 410 that further terminates into a top portion 420. The tubular shaped covering 410 includes a front portion 430, a back portion 440, and a pair of side portions 450. The front portion 430 extends inwardly from the base 400 to a concave section 432. The back portion 440 also extends inwardly from the base 400 to a concave section 440. The termination from the tubular shaped covering 410 to the top portion 420 is slightly bent from the axis of the tubular shaped covering. The angle defined by the bending is a and is preferably about 25°-35°. Internally the shroud 160 may include an annular flange 460 approximately near the base portion 400 termination to the tubular shaped covering. The flange 460 extend radially inward and act as a stop when the shroud 160 is inserted over the shoulder section 155 of the secondary casing 150. Lastly, the shroud 160 may include a ribbed or flexible end 470 below the base 400 such that it may be secured to the secondary casing by tightly fitting the flexible end over the end of the secondary casing.

From the foregoing and as mentioned above, it will be observed that numerous variations and modifications may be effected without departing from the spirit and scope of the novel concept of the invention. It is to be understood that no limitation with respect to the specific methods and apparatus illustrated herein is intended or should be inferred.

I claim:

1. A light therapy apparatus comprising:
   a main casing having front and rear ends;
   a front cap having a central bore and having a threaded internal structure for securing the front cap to corresponding threaded external structure on the front end of the main casing;
   a secondary casing having a base end positioned within the front cap and over the front end of the main casing, the secondary casing further including a shoulder section extending outwardly from the base end out of the front cap;
   a light source having one end secured within the main casing and having a length such that a second end defined by the light source extends through the central bore of the front cap and through the secondary casing such that the light source includes a portion exposed out of the secondary casing;
   a shroud placed over the exposed portion of the light source and having at least a flexible bottom end for tightly fitting over an end of the shoulder section, the shroud further includes a rigid portion extending from the flexible bottom end and extending for a remaining portion of the shroud such that the rigid portion covers the exposed portion of the light source and at least the rigid portion being made of a light-resistance material;
   a lens positioned in an aperture defined through the shroud such that light from the light source unable to penetrate the light-resistance material of the shroud is capable of exiting the shroud through the lens; and
   a fan positioned within the main casing and directed to transmit air flow to the shroud;
   wherein the light source and the shroud each include a top portion bent away from a base portion at an angle of about 25-35°.

2. The apparatus of claim 1, wherein the main casing includes an air intake aperture.

3. The apparatus of claim 1, wherein the shroud further includes an air exhaust aperture.

4. The apparatus of claim 1 further comprising a cooling tube to direct air flow from the casing into the shroud, the cooling tube includes a first opened end positioned within the casing and includes a second opened end positioned within the shroud.

5. The apparatus of claim 4 further comprising a heat output tube to direct air flow from the shroud to an exhaust outlet defined in the casing.

6. The apparatus of claim 1, wherein the shroud is defined as having a base portion extending upwardly to form an elliptically tubular shaped covering that terminates into a top portion, the elliptically tubular shaped covering includes a front portion, a back portion, and a pair of side portions, the front portion extends inwardly from the base to a concave section, and the back portion extends inwardly from the base to a concave section.

7. The apparatus of claim 6, wherein the shroud further includes internally defined annular flange extending radially inward and will come into contact with the shoulder section when the shroud is placed thereover.

8. A light therapy apparatus comprising:
   a main casing having front and rear ends;
   a front cap having a central bore and having a threaded internal structure for securing the front cap to corresponding threaded external structure on the front end of the main casing;
   a secondary casing having a base end positioned within the front cap and over the front end of the main casing, the secondary casing further including a shoulder section extending outwardly from the base end out of the front cap;
   a light source having one end secured within the main casing and having a length such that a second end defined by the light source extends through the central bore of the front cap and through the secondary casing such that the light source includes a portion exposed out of the secondary casing;
   a shroud placed over the exposed portion of the light source and having at least a flexible bottom end for tightly fitting over an end of the shoulder section, the shroud further includes a rigid portion covering the exposed portion of the light source and being made of a light-resistance material;
   a lens positioned in an aperture defined through the shroud such that light from the light source unable to penetrate the light-resistance material of the shroud is capable of exiting the shroud through the lens; and
   a fan positioned within the main casing and directed to transmit air flow to the shroud and wherein the shroud further includes an air exhaust aperture to reduce the internal temperature of the shroud;
   wherein the light source and the shroud each include a top portion bent away from a base portion at an angle of about 25-35°.

9. The apparatus of claim 8, wherein the shroud is defined as having a base portion extending upwardly to form an elliptically a tubular shaped covering that terminates into a top portion, the elliptically tubular shaped covering includes a front portion, a back portion, and a pair of side portions, the front portion extends inwardly from the base to a concave section, and the back portion extends inwardly from the base to a concave section.

10. The apparatus of claim 9, wherein the shroud further includes internally defined annular flange extending radially inward and will come into contact with the shoulder section when the shroud is placed there over.

* * * * *